US006344338B1

(12) United States Patent
Bowen et al.

(10) Patent No.: US 6,344,338 B1
(45) Date of Patent: *Feb. 5, 2002

(54) DEPOSIT ASSESSMENT OF *BACILLUS THURINGIENSIS* DELTA-ENDOTOXIN

(75) Inventors: A. Temple Bowen, Milford, CT (US); Penny L. Hunst, Woodland; Jennifer K. Swank, Elk Grove, both of CA (US)

(73) Assignee: Valent BioSciences Corporation, Libertyville, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 30 days.

(21) Appl. No.: 08/944,709

(22) Filed: Oct. 6, 1997

Related U.S. Application Data

(63) Continuation of application No. 08/320,797, filed on Oct. 11, 1994, now abandoned.

(51) Int. Cl.[7] ................... G01N 33/554; G01N 33/569; G01N 33/53; G01N 33/567
(52) U.S. Cl. ................... 435/7.32; 435/7.92; 435/7.93; 435/7.94; 435/7.95; 435/810; 436/503; 436/512; 436/518; 436/531; 436/538; 436/540; 436/543; 436/546
(58) Field of Search ................ 435/7.32, 7.92, 435/7.93, 7.94, 7.95, 810; 436/503, 512, 518, 531, 538, 540, 543, 546

(56) References Cited

U.S. PATENT DOCUMENTS 4,780,408 A * 10/1988 Dunbar et al.
5,279,962 A *  1/1994 Gurtler et al.
5,695,928 A * 12/1997 Stewart
5,747,450 A *  5/1998 Ohba et al.

FOREIGN PATENT DOCUMENTS

WO      9105259   *  4/1991
WO      9523847       9/1995

OTHER PUBLICATIONS

Palm et al. "Quantification in Soil of B.&. K δendotoxin . . . " Mol. Ecol. 1994, 3(2), 145–51.*

Spinks et al. "Production and Characterization of mAb . . . " Food & Agric. Immunol. (1993) 5, 13–25.*

Hock et al. "Toxicity Assessment . . . " Environ. Toxic. & Water Quality: An Int'l. T. vol. 9 (1994) 243–262.*

Muldoon et al. "Evaluation of Elisa for . . . " J. Agric. Food Chem 41(2) 1993 322–78.*

Cikonek et al. "Immunochemical Determination . . . " Rostl. Vyroba (1993) 39(2), 149–56.*

Beard Et Al (J. of Chromatography vol. 589, pp 265–270), 1992.*

Chemical Abstracts, vol. 19, No. 7, Abstract No. 65511, p. 363, Columbus, OH, Aug. 16, 1993.

M. Huber–Lukas, et al., Experientia, 38:1103–1105, 1982.

* cited by examiner

*Primary Examiner*—Mark Navarro
(74) *Attorney, Agent, or Firm*—Rockey, Milnamow & Katz, Ltd.

(57) ABSTRACT

The invention relates to an immunochemical method for detecting deposit of *Bacillus thuringiensis* delta-endotoxin or pesticidally-active fragment thereof on a plant or tree. The invention further relates to kits for using such a method.

11 Claims, 1 Drawing Sheet

FIG. 1

PERFORMANCE OF DAM KIT IN DETERMINING
CONCENTRATION OF FORAY 48B SPRAYED ON
OAK LEAVES.

FORAY 48B (ng/leaf) vs DROPS FORAY 48B/Leaf

● PREDICTED   $R^2 = 1.00$
○ KIT         $R^2 = 0.90$

DEPOSIT ASSESSMENT OF *BACILLUS THURINGIENSIS* DELTA-ENDOTOXIN

This application is a Continuation of application Ser. No. 08/320,797 filed Oct. 11, 1994 now abandoned.

1. FIELD OF THE INVENTION

The invention relates to an immunochemical method for detecting the deposit of *Bacillus thuringiensis* delta-endotoxin or pesticidally-active fragment thereof on a plant or tree. The invention further relates to kits for using such a method.

2. BACKGROUND OF THE INVENTION

*Bacillus thuringiensis* is the most widely used biopesticide. *Bacillus thuringiensis* is a motile, rod-shaped, gram-positive bacterium that is extensively distributed in nature, especially in soil and insect-rich environments. During sporulation, *Bacillus thuringiensis* produces a parasporal crystal inclusion(s) which is insecticidal upon ingestion to suceptible insect larvae of the orders Lepidoptera, Diptera, and Coleoptera. The inclusions may vary in shape, number, and composition. They are comprised of one or more proteins called delta-endotoxins, which may range in size from 27–140 kDa. The insecticidal delta-endotoxins are generally converted by proteases in the larval gut into smaller (truncated) toxic polypeptides, causing midgut destruction, and ultimately, death of the insect (Höfte and Whiteley, 1989, *Microbiological Reviews* 53:242–255).

There are several *Bacillus thuringiensis* strains that are used as bioinsecticides in the forestry, agricultural, and public health areas. *Bacillus thuringiensis* subsp. *kurstaki* and *Bacillus thuringiensis* subsp. *aizawai* produce delta-endotoxins specific for Lepidoptera. A delta-endotoxin specific for Coleoptera is produced by *Bacillus thuringiensis* subsp. *tenebrionis* (Krieg et al., 1988, U.S. Pat. No. 4,766,203). Furthermore, *Bacillus thuringiensis* subsp. *israelensis* produces delta-endotoxins specific for Diptera (Goldberg, 1979, U.S. Pat. No. 4,166,112).

The delta-endotoxins are encoded by cry (crystal protein) genes which are generally located on plasmids. The cry genes have been divided into six classes and several subclasses based on relative amino acid homology and pesticidal specificity. The major classes are Lepidoptera-specific (cryI); Lepidoptera-and Diptera-specific (cryII); Coleoptera-specific (cryIII); Diptera-specific (cryIV) (Höfte and Whiteley, 1989, *Microbiological Reviews* 53:242–255); Coleoptera- and Lepidoptera-specific (referred to as cryV genes by Tailor et al., 1992, *Molecular Microbiology* 6:1211–1217); and Nematode-specific (referred to as cryV and cryVI genes by Feitelson et al., 1992, *Bio/Technology* 10:271–275).

Delta-endotoxins have been produced by recombinant DNA methods. The delta-endotoxins produced by recombinant DNA methods may or may not be in crystal form.

The deposition of a delta-endotoxin onto a plant or tree by application, particularly by aerial application, is complicated by a number of factors including canopy architecture of the plants or trees, meteorological conditions, dilution of the delta-endotoxin formulation, and atomization of the delta-endotoxin formulation during application. In forestry, it is estimated that the deposit efficiency is in the range of 10–50% of the emitted volume in the application of Bacillus thuringiensis delta-endotoxin formulations.

A specific problem in the art is to assess directly the extent of coverage or deposit of a delta-endotoxin after the delta-endotoxin is applied to a plant or tree to control a destructive pest. This assessment is very important for preventing the pesticidal destruction of a plant or tree by alerting the applicator that further application of the delta-endotoxin is needed.

The art has had a long felt, but unfulfilled need for a method that would allow the direct measurement of a delta-endotoxin deposited on a plant or tree by being able to take samples of leaves from plants in a field or from trees in a forest, and directly measuring the deposit of the delta-endotoxin on the leaf, as well as delta-endotoxin deposited on tree bark. Fulfillment of this need would be very advantageous in the art since it would allow the direct determination of the extent of coverage of a delta-endotoxin, and, furthermore, provide an indication of the need for follow-up applications in areas not sufficiently covered to prevent destruction by a pest.

Generally, the activity of *Bacillus thuringiensis* delta-endotoxin is determined by bioassay. Specifically, the delta-endotoxin is incubated with its target pest, and the increase in mortality and/or stunting of growth of the insect is determined. However, there are a number of disadvantages to bioassays. Bioassay is a labor intensive, time consuming process with a low capacity for sample throughput for quantitative analyses. It requires the rearing of the target species and maintaining a constant colony which is healthy and will perform consistently in the assays. Additionally, since insects are biological organisms, they are prone to the variability that accompanies the use of biological organisms in an assay system —+/−20%. These disadvantages preclude the use of bioassay in assessing the deposit of a *Bacillus thuringiensis* delta-endotoxin.

A dye incorporated into the pesticidal formulation prior to application can be used as an indirect marker for determining deposition. However, the use of a dye marker for determining deposit is limited in that it can be used only under experimental test conditions and for relatively small application areas. Furthermore, spray cards for measuring the deposit are used which requires significant effort in placing the cards prior to application and in analyzing the cards following application. Dye incorporation is, therefore, not a practical way for determining deposit.

In the prior art, polyclonal and monoclonal antibodies have been generated that specifically react with delta-endotoxin. Polyclonal antibodies have been obtained to the delta-endotoxins of a number of subspecies of *Bacillus thuringiensis* (Krywienzzcyk, 1977, Publication 1P-X-16, Insect Pathology Research Institute, Canadian Forest Service, Sault Sainte Marie, Ontario, Canada). Monoclonal antibodies have been obtained to the delta-endotoxin of *Bacillus thuringiensis* subsp. *kurstaki* (Huber-Lukac et al., 1986, *Infection and Immunity* 54:228–232; Groat et al., in Analytical Chemistry of *Bacillus thuringiensis*, ACS Symposium Series 432, Leslie A. Hickle and William L. Fitch, eds., 1990, pp. 88–97), *Bacillus thuringiensis* subsp. *thuringiensis* (Huber-Lukac et al., 1982, *Experentia* 38:1103–1105), *Bacillus thuringiensis* subsp. *berliner* (Höfte et al., 1988, *Appl. Environ. Microbiol.* 54:2010–2017) and *Bacillus thuringiensis* subsp. *israelensis* (U.S. Pat. No. 4,945,057). However, a practical and reliable method for assessing deposit of a *Bacillus thuringiensis* delta-endotoxin has not resulted from the availability of these antibodies.

It is an object of the present invention to provide an immunochemical method and kits thereof for assessing directly the deposition of a *Bacillus thuringiensis* delta-endotoxin after the delta-endotoxin is applied to a plant or tree for controlling a pest.

3. SUMMARY OF THE INVENTION

The present invention is directed to an immunochemical method that satisfies the need to directly measure the deposition of a *Bacillus thuringiensis* delta-endotoxin or pesticidally-active fragment thereof on a plant or tree. Said method comprises (a) isolating the delta-endotoxin from said sample; (b) reacting the isolated delta-endotoxin of step (a) with at least one antibody or $Fab_1$, $F(ab')_2$, or $F_v$ fragment thereof, in which said antibody binds specifically to the delta-endotoxin; and (c) observing the presence or absence of binding of the antibody of step (b) to said delta-endotoxin. The amount of delta-endotoxin present on the sample may be determined by comparing the amount of binding of the *Bacillus thuringiensis* delta-endotoxin in the sample to the antibody of step (b) to the amount of binding of a known amount of *Bacillus thuringiensis* delta-endotoxin to said antibody.

In a specific embodiment, the sample is reacted with two antibodies. In one embodiment, one antibody is a polyclonal antibody specific to a *Bacillus thuringiensis* delta-endotoxin or pesticidally-active fragment thereof. In another embodiment, the one antibody is a monoclonal antibody specific to a *Bacillus thuringiensis* delta-endotoxin or pesticidally-active fragment thereof. In another embodiment, the other antibody is a polyclonal antibody specific to a *Bacillus thuringiensis* delta-endotoxin or pesticidally-active fragment thereof. In another embodiment, the other antibody is a monoclonal antibody specific to a *Bacillus thuringiensis* delta-endotoxin or pesticidally-active fragment thereof. In a preferred embodiment, both antibodies are polyclonal antibodies specific to the delta-endotoxin or pesticidally-active fragment thereof from *Bacillus thuringiensis* subsp. *kurstaki*.

The invention is also directed to a kit for detecting a *Bacillus thuringiensis* delta-endotoxin or pesticidally-active fragment thereof deposited on a sample from a plant or tree. Such a kit comprises (a) an extraction buffer for isolating the delta-endotoxin from said sample; and (b)at least one antibody or $Fab_1$, $F(ab')_2$, or $F_v$ fragment thereof, in which said antibody binds specifically to the delta-endotoxin. In one embodiment, the antibody may be attached to a solid support. The kit may also comprise a second antibody which is labeled with a reporter molecule. Furthermore, the kit may also comprise a standard delta-endotoxin or pesticidally-active fragment thereof of known amount.

4. BRIEF DESCRIPTION OF THE FIGURE

These and other features, aspects, and advantages of the present invention will become better understood with reference to the following description, appended claims, and accompanying figure where:

FIG. 1 shows a determination of the concentration of Foray™ 48B applied to oak leaves.

5. DETAILED DESCRIPTION OF THE INVENTION

The method of the present invention may be used for detecting the deposit on a sample from a plant or tree of a *Bacillus thuringiensis* delta-endotoxin or a pesticidally-active fragment thereof including, but not limited to, *Bacillus thuringiensis* subsp. *kurstaki*, *Bacillus thuringiensis* subsp. *aizawai*, *Bacillus thuringiensis* subsp. *galleriae*, *Bacillus thuringiensis* subsp. *entomocidus*, *Bacillus thuringiensis* subsp. *tenebrionis*, *Bacillus thuringiensis* subsp.*alesti*, *Bacillus thuringiensis* subsp. *canadiensis*, *Bacillus thuringiensis* subsp. *darmstadiensis*, *Bacillus thuringiensis* subsp. *dendrolimus*, *Bacillus thuringiensis* subsp. *finitimus*, *Bacillus thuringiensis* subsp. *kenyae*, *Bacillus thuringiensis* subsp. *morrisoni*, *Bacillus thuringiensis* subsp. *subtoxicus*, and *Bacillus thuringiensis* subsp. *toumanoffi*. More specifically, the *Bacillus thuringiensis* delta-endotoxin or pesticidally-active fragment thereof may be selected from the group including, but not limited to, CryI, CryII, CryIII, CryIV, CryV, and CryVI. In a preferred embodiment, the *Bacillus thuringiensis* delta-endotoxin or pesticidally-active fragment thereof is *Bacillus thuringiensis* subsp. *kurstaki* delta-endotoxin or pesticidally-active fragment thereof. In a more preferred embodiment, the delta-endotoxin is a CryI protein.

The method of the present invention may be used to determine the deposit of a *Bacillus thuringiensis* (B.t.) delta-endotoxin or pesticidally-active fragment thereof on a sample from a plant or tree, e.g., leaf or bark, whereon a B.t. formulation comprising delta-endotoxin or pesticidally active fragment thereof is applied to control a pest from destruction of the plant or tree by a pest. Examples of such plants and trees include, but are not limited to, deciduous trees and conifers (e.g., linden, yew, oak, alders, poplar, birch, fir, larch, pine); drupes, pomes, and soft fruit (e.g., apples, pears, plums, peaches, almonds, walnuts, peanuts, cherries, strawberries, raspberries, and blackberries); leguminous plants (e.g., alfalfa, beans, lentils, peas, soybeans); fibre plants (e.g., cotton, flax, hemp, jute); citrus fruit (e.g., oranges, lemons, grapefruit, mandarins); oil plants (e.g., rape, mustard, poppy, olives, sunflowers, coconuts, castor oil, cocoa bean, groundnuts); cucumber plants (e.g., cucumber, marrows, melons); cereals (e.g., wheat, barley, rye, oats, rice, sorghum, and related crops); lauraceae (e.g., avocados, cinnamon, camphor); beets (e.g., sugar beet and fodder beet); vegetables (e.g., spinach, lettuce, asparagus, cabbages, other brassicae, carrots, onions, potatoes, and tomatoes); or plants such as maize, turf plants, nuts, coffee, sugar cane, tea, vines, hops, bananas, and natural rubber plants, as well as ornamentals.

5.1. Isolation of Delta-Endotoxin

The delta-endotoxin or pesticidally-active fragment thereof may be isolated from a sample of a plant or tree, e.g., leaf or bark, by solubilization of the delta-endotoxin or pesticidally-active fragment thereof in an extraction buffer. In a preferred embodiment, the buffer has an alkaline pH, most preferably with a pH in the range of about 9.5 to about 12.5. The buffer may comprise a reagent(s) that includes, but is not limited to, sodium hydroxide, tribasic phosphate, sodium borate and sodium carbonate. The buffer may also comprise a reducing agent which preferably has a pH of about 8.0 to about 9.5. Examples of such reducing agents include, but are not limited to, beta-mercaptoethanol, dithioerythritol, and dithiothreitol. The extraction time can vary from about 0.25 hour to about 8hours, but more preferably is about 1.5 to about 3.0 hours, and most preferably is about 2 hours. The temperature for extraction of the delta-endotoxin or pesticidally-active fragment thereof can be in the range of about 15° C. to about 32° C., but more preferably is in the range of about 20° C. to about 25° C. Following extraction of the delta-endotoxin or pesticidally active fragment thereof, the extracted solution may be neutralized with a buffer with a pH in the range of about 6 to about 8, but more preferably to a pH in the range of about 6.5 to about 7.5, and most preferably to a pH in the range of about 6.9 to about 7.1. The neutralization buffer may be phosphate-buffered saline. Alternatively, the buffer may comprise phosphate buffer or hydrochloric acid.

5.2. Antibodies

The antibodies used in the method of the present invention may be polyclonal and/or monoclonal antibodies.

The production of a polyclonal antibody may be conducted as described infra. Any hemothermic animal can serve as a source of immune serum. Rabbits are preferred in the art to produce immune serum because they yield adequate volumes of high-titered serum in return for relatively small amounts of antigen used for immunization. Intramuscular or intravenous injection may be used.

In a specific embodiment, immunization may be initiated by injecting a rabbit with about 100 ul of an emulsion containing about 1 to about 5 mg of delta-endotoxin protein antigen per ml of 0.1 M sodium chloride-15 mM sodium azide plus an equal volume of incomplete Freund's adjuvant. Further doses of antigen are injected at 14, 28, and 42 days, and thereafter, at 4 week intervals. It is preferable to use at least 4 rabbits to ensure sufficient antibodies are produced against the antigen.

At 28 days, 20–40 ml of blood are withdrawn from a peripheral vein in each rabbit's ear. The crude serum is analyzed to determine whether antibody is being produced. Analysis of the antibody preparation s is conducted using immunochemical methods known in the art (Axelsen, Nils H. [ed.], Handbook of Immunoprecipitation-In-Gel Techniques, Scandinavian Journal of Immunology Supplement No. 10, Volume 17, 1983, Blackwell Scientific Publications, Oxford, England; Hames, B. D. and Rickwood, D., D. Gel Electrophoresis of Proteins, A Practical Approach, IRL Press Limited, 1981, Oxford, England).

On day 50, 45–50 ml of blood are drawn from each rabbit. Further, 50 ml aliquots are taken at 2 week intervals. This schedule of immunization (4 week intervals) and bleeding (2 week intervals) can be continued for prolonged periods without harm to the rabbits. This procedure is usually carried out until approximately 200 ml of serum have been collected.

Purification of the serum is conducted to remove any proteases that may degrade the antibodies in the serum using methods known in the art such as ammonium sulfate precipitation and size exclusion chromatography, e.g., Sephadex G50.

The production of a monoclonal antibody may be conducted as described infra. Mice are injected with a protein cocktail comprising between about 50 to about 100 $\mu$g of Bacillus thuringiensis delta-endotoxin. The delta-endotoxin may be combined with an adjuvant (e.g. Freund's, lipopolysaccharide, aluminum hydroxide). The program for inoculation is not critical and may be any normally used for this purpose in the art. Such procedures are described, for example, in E. Harlow and D. Lane, Antibodies: A Laboratory Manual, Cold Spring Harbor, 1988.

Fusion procedures for creation of hybridomas are well known in the art, and any of the known procedures are useful for the production of the hybridomas of the present invention. The basic procedure generally is that developed by Kohler and Milstein (1975, Nature 256:495) and Hammerling (1977, Eur. J. Immunol. 7:743). Other techniques which have recently become available, such as the human B-cell hybridoma technique (Kozbor et al., 1983, immunology Today 4:72) and EBV-hybridoma technique (Cole et al., 1985, Monoclonal Antibodies and Cancer Therapy, Alan R. Liss, Inc., pp. 77–96) are within the scope of the present invention.

Spleen cells (or alternatively, peripheral blood lymphocytes) are isolated from the immunized animal and the number of cells counted.

At about two weeks after fusion, culture supernatant is tested for the presence of antibody to Bacillus thuringiensis delta-endotoxin. A number of different serologic and biochemical tests are known for evaluating antibodies secreted by various hybridomas. In a preferred manner, a modified enzyme-linked immunosorbent assay is used.

In order to determine the degree of specificity of the selected monoclonal antibodies, it is desirable to screen them against delta-endotoxins of other subspecies of Bacillus thuringiensis. For example, if an antibody is obtained against the delta-endotoxin of Bacillus thuringiensis subsp. kurstaki, the antibody should be tested against, for example, the delta-endotoxin of Bacillus thuringiensis subsp. israelensis.

5.3. Immunoassays

The antibodies used in the method of the present invention may be employed as the basic reagents in a number of different immunoassays to determine the presence of a Bacillus thuringiensis delta-endotoxin or pesticidally-active fragment thereof on a plant or tree. Generally speaking, the antibodies can be employed in any type of immunoassay, whether qualitative or quantitative. The type of immunoassay includes both single site and two-site or sandwich, assays of the non-competitive type, as well as in traditional competitive binding assays.

Particularly preferred, for ease of detection, and its quantitative nature, is the sandwich or double antibody assay, of which a number of variations exist, all of which are intended to be encompassed by the present invention.

For example, in a typical assay, unlabeled or antibody labeled with a reporter molecule, described infra, is immobilized on a solid substrate and the sample to be tested is brought into contact with the bound molecule after a suitable period of incubation, for a period of time sufficient to allow formation of an antibody-delta-endotoxin binary complex. The solid substrate may, for example, be glass or a polymer including, but not limited to, cellulose, polyacrylamide, nylon, polystyrene, polyvinyl chloride or polypropylene. The solid substrates may be in the form of tubes, beads, discs, or microplates, or any other surface suitable for conducting an immunoassay.

After unbound material is washed away, a second antibody, labeled with a reporter molecule capable of inducing a detectable signal, is then added and incubated, allowing sufficient time for the formation of a ternary complex of antibody-delta-endotoxin-labeled antibody. The term "reporter molecules", as used herein means a molecule which by its chemical nature, provides an analytically detectable signal which allows detection of delta-endotoxin-bound antibody. Any unreacted material is washed away, and the presence of the delta-endotoxin is determined by observation of a signal, or may be quantitated by comparing with a standard sample containing known amounts of delta-endotoxin.

The most commonly used reporter molecules in this type of assay are either enzymes, fluorophores, or radionuclide-containing molecules. In the case of an enzyme immunoassay, an enzyme is conjugated to the second antibody, sometimes by means of glutaraldehyde or periodate. As will be readily recognized, a wide variety of different conjugation techniques exist, which are well-known to the skilled artisan. Commonly used enzymes include but are not limited to horseradish peroxidase, glucose oxidase, beta-galactosidase and alkaline phosphatase. The substrates to be used with the specific enzymes are generally chosen for the production, upon hydrolysis by the corresponding enzyme, or a detectable color change. For example, p-nitrophenyl phosphate is suitable for use with alkaline phosphatase conjugates; for peroxidase conjugates, 1,2-phenylenediamine or toluidine is commonly used. It is also possible to employ fluorogenic substrates, which yield a fluorescent product rather than the chromogenic substrates noted above. In all cases, the enzyme-labeled antibody is added to the first antibody-delta-endotoxin complex, allowed to bind to the complex, and excess reagent is washed away. A solution containing the appropriate substrate is then added to the tertiary complex of antibody-delta-endotoxin-labeled antibody. The substrate reacts with the enzyme linked to the second antibody, giving a qualitative visual signal, which may be further quantitated, usually spectrophotometrically, to give an evaluation of the amount of delta-endotoxin which is present in the sample.

Alternatively, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. As in enzyme immunoassay, the fluorescent labeled PLF (phycobiliprotein fluorochrome)-specific antibody is allowed to bind to the first antibody-ferritin complex. After washing of the unbound reagent, the remaining ternary complex is then exposed to light of the appropriate wavelength, and the fluorescence observed indicates the presence of the delta-endotoxin of interest. Immunofluorescence and enzyme immunoassay techniques are both very well established in the art and are particularly preferred for the present method. However, other reporter molecules, such as radioisotopes, chemiluminescent, or bioluminescent molecules may also be employed. It will be readily apparent to those skilled in the art how to vary the procedure to suit the required use.

Variations on the forward assay include the simultaneous assay, in which both sample and antibody are added simultaneously to the bound antibody, or a reverse assay in which the labeled antibody and sample to be tested are first combined, incubated, and added to the unlabeled surface bound antibody. In an alternative embodiment, the delta-endotoxin sample may be bound to the solid surface and subsequently reacted with an antibody. It is then reacted with a second general antibody (labeled) and the signal is detected. In yet another embodiment, a known amount of *Bacillus thuringiensis* delta-endotoxin as a standard is bound to the solid support. Sample and antibodies are subsequently added. These techniques are well known to those skilled in the art, and the possibility of minor variations will be readily apparent. As used herein, "sandwich assay" is intended to encompass all variations on the basic two-site technique.

In the method of the invention for detecting *Bacillus thuringiensis* delta-endotoxin or pesticidally-active fragment thereof deposited on a plant or tree, the only limiting factor is that at least one antibody be specific for the delta-endotoxin or pesticidally-active fragment thereof. Thus, a number of possible combinations are possible. For example, one antibody may be polyclonal, and the other a monoclonal antibody. Alternatively, one antibody, may be a general antibody which is non-specific in nature (e.g. goat anti-mouse IgG), while the other antibody is the antibody which is specific to the delta-endotoxin or pesticidally-active fragment thereof. Also, both antibodies may be specific for the *Bacillus thuringiensis* delta-endotoxin or pesticidally-active fragment thereof. In another embodiment, both antibodies are the same polyclonal antibody that is specific for the delta-endotoxin or pesticidally-active fragment thereof from *Bacillus thuringiensis* subsp. *kurstaki*.

5.4. Kits

The present invention further relates to an immunochemical kit incorporating the method of the present invention described supra for detecting a *Bacillus thuringiensis* delta-endotoxin or pesticidally-active fragment thereof deposited on a plant or tree. The kit comprises an extraction buffer described in Section 5.1., supra for extracting the delta-endotoxin or pesticidally-active fragment thereof from a sample of a tree or plant, e.g. leaf or bark, and an antibody which binds specifically to the delta-endotoxin or pesticidally-active fragment thereof. The kit may also comprise a neutralization buffer described in Section 5.1., supra.

The kit of the present invention may further comprise a *Bacillus thuringiensis* delta-endotoxin or pesticidally-active fragment thereof standard for comparing the amount of binding of the extracted delta-endotoxin or pesticidally-active fragment thereof to the first antibody to the amount of binding of a known amount of the delta-endotoxin or pesticidally-active fragment thereof as a standard to the first antibody. In another embodiment, the delta-endotoxin or pesticidally-active fragment thereof standard is a *Bacillus thuringiensis* subsp. *kurstaki* delta-endotoxin or pesticidally-active fragment thereof. In a preferred embodiment, the standard is FORAY™ 48B with a potency of about 12,000,000 IU per ml.

The kit may further comprise a second antibody. In a specific embodiment, the kit comprises an antibody bound to a solid support and an antibody labeled with a reporter molecule, in which both antibodies react with the delta-endotoxin or pesticidally-active fragment thereof. In a preferred embodiment, the antibody bound to the solid support is a polyclonal antibody that is specific to the delta-endotoxin proteins from *Bacillus thuringiensis* subsp. *kurstaki*. The polyclonal antibody reacts with the CryIA(a), CryIA(b), CryIA(c), and CryII proteins. In a preferred embodiment, the solid support is a test strip in a microtiter plate format. In another preferred embodiment, the antibody labeled with a reporter molecule is the same polyclonal antibody that is specific to the delta-endotoxin proteins from *Bacillus thuringiensis* subsp. *kurstaki*. The reporter molecule can be any of the molecules described supra. In a preferred embodiment, the reporter molecule is horseradish peroxidase conjugated to the polyclonal antibody.

The following examples are presented by way of illustration, not by way of limitation.

6. EXAMPLES

6.1. Application of Foraym 48B to Leaves

Droplets of 100 µ of Foray™ 48B (*Bacillus thuringiensis* subsp. *kurstaki*; obtained from Novo Nordisk A/S) were applied to oak leaves in known numbers of droplets ranging from 0 to 90 drops per leaf. Each droplet was estimated to contain 100 ng of Foray™ 48B. Each leaf was then allowed to air dry.

6.2. Extraction of Foray™ 48B from a Leaf

Each oak leaf sample applied with Foray™ 48B as described in Section 6.1. was placed into a small plastic bag and soaked in 5 ml of 0.125 M tribasic phosphate pH 12.1 for 2 hours at 22° C. to extract the delta-endotoxin of Foray™ 48B from the surface of the leaf. The surface area of the leaf samples was 80 cm². A volume of 0.5 ml of each extracted delta-endotoxin was combined with 0.5 ml of phosphate buffered saline (0.1 M phosphate, pH 2.0) as a neutralizing buffer. Samples of Foray™ 48B as a standard were also solubilized using 0.125 M tribasic phosphate pH 12.1 using the procedure described in Section 6.1.

6.3. Deposit Immunoassay

Two droplets or 0.1 ml of each extracted neutralized sample as described in Section 6.2 was added to selected wells in a test strip which contains bound *Bacillus thuringiensis* subsp. *kurstaki* polyclonal antibody. Two drops of enzyme conjugate, polyclonal *Bacillus thuringiensis* subsp. *kurstaki* antibody conjugated to horseradish peroxidase, were added to each sample well. The test strip was then incubated for 1 hour. A negative control was run using two droplets or 0.1 ml of the neutralization buffer. A standard curve was also run by using the standard Foray™ 48B samples in Section 6.2 and placing two droplets or 0.1 ml of each sample into a well.

The test strip was washed with water five times to remove all residual plant material. The wells were filled with 0.3 ml of phosphate-buffered saline with Tween™ 80 (Sigma Chemical Company, St. Louis, Mo.) wash solution. The wells were emptied and filled with four drops or 0.2 ml of substrate solution comprised of tetramethylbenzidine and hydrogen peroxide and incubated for 15 minutes.

The amount of deposited Foray™ 48B was determined visually by comparison to that part of the test strip containing Foray™ 48B as a standard. The amount of Foray™ 48B can also be determined spectrophotometrically at 650 nm. For very sensitive detection, 1 drop of 3 M sulfuric acid is added to each well and the color detected at 450 nm.

The results, as shown in FIG. 1, demonstrated that there was a very good correlation between the predicted and detected amounts of Foray™ 48B deposited on each leaf. Amounts are predicted by weight. Specifically, a 100 um droplet is equivalent to 100 ug. This method can be used to detect Foray™ 48B in the range of 2 ng/ml to 400 ng/ml.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for detecting the amount of *Bacillus thuringiensis* delta-endotoxin or pesticidally active fragment thereof in a sample from a non-transgenic plant or tree comprising:

(a) obtaining a sample containing a delta-endotoxin from a non-transgenic plant or tree;

(b) isolating the delta-endotoxin from the sample by incubating the sample in an extraction buffer having a pH in the range of from about 9.5 to about 12.5 for a period of from about 1.5 hours to about 3.0 hours and at a temperature of from about 15° C. to about 32° C.;

(c) reacting the isolated delta-endotoxin of step (b) with at least one antibody or $Fab_1$, $F(ab')_2$, or $F_v$ fragment thereof, in which said antibody binds specifically to the delta-endotoxin;

(d) determining the amount of binding of the antibody of step (c) to said delta-endotoxin; and (e) comparing the amount of binding of the *Bacillus thuringiensis* delta-endotoxin in the sample to the antibody in step (c) to the amount of binding of a known amount of *Bacillus thuringiensis* delta-endotoxin to said antibody.

2. The method of claim 1 wherein said sample is a leaf sample.

3. The method of claim 1 wherein said sample is a bark sample from a tree.

4. The method of claim 1 wherein a neutralization buffer is added in step (b) after incubating said sample in said extraction buffer.

5. The method of claim 4 wherein said neutralization buffer has a pH of about 6 to about 8.

6. The method of claim 1 wherein said isolated delta-endotoxin is reacted with an antibody in step (c) and wherein said antibody is a polyclonal antibody.

7. The method of claim 1 wherein said *Bacillus thuringiensis* delta-endotoxin is a *Bacillus thuringiensis* subsp. *kurstaki* delta-endotoxin.

8. The method of claim 1 wherein said isolated delta-endotoxin is reacted with an antibody in step (c) and wherein said antibody is a monoclonal antibody.

9. The method of claim 1 wherein two antibodies are reacted with said isolated delta-endotoxin in step (c).

10. The method of claim 9 wherein one of the two antibodies is labeled with a reporter molecule.

11. The method of claim 1 wherein said period of step (b) is about 2 hours.

* * * * *